(12) United States Patent
Egorov

(10) Patent No.: US 6,232,091 B1
(45) Date of Patent: May 15, 2001

(54) ELECTROOPTICAL APPARATUS AND METHOD FOR MONITORING CELL GROWTH IN MICROBIOLOGICAL CULTURE

(75) Inventor: Vladimir Egorov, Plainsboro, NJ (US)

(73) Assignee: Artann Laboratories, Lambertville, NJ (US)

( * ) Notice: Subject to any disclaimer, the term of this patent is extended or adjusted under 35 U.S.C. 154(b) by 0 days.

(21) Appl. No.: 09/371,810

(22) Filed: Aug. 11, 1999

(51) Int. Cl.[7] .............................. C12Q 1/02; C12M 1/00

(52) U.S. Cl. ........................................ 435/29; 435/283.1

(58) Field of Search .................................. 435/29, 283.1

(56) References Cited

U.S. PATENT DOCUMENTS

| | | |
|---|---|---|
| 3,933,592 | 1/1976 | Clendenning ........................... 435/29 |
| 4,250,894 | 2/1981 | Frei et al. ................................ 435/29 |
| 4,515,274 | 5/1985 | Hollinger et al. ...................... 435/29 |
| 4,576,916 | 3/1986 | Lowke et al. .......................... 435/29 |
| 4,661,845 | 4/1987 | Saito et al. .............................. 435/29 |
| 4,893,935 | 1/1990 | Mandel et al. .......................... 435/29 |
| 5,099,848 | 3/1992 | Parker et al. ............................ 435/29 |
| 5,141,869 | 8/1992 | Steele et al. ............................ 435/29 |
| 5,178,148 | 1/1993 | Lacoste et al. ......................... 435/29 |
| 5,265,612 | 11/1993 | Sarvazyan et al. ..................... 435/29 |
| 5,344,535 * | 9/1994 | Betts et al. ......................... 435/283.1 |
| 5,408,307 | 4/1995 | Yamamoto et al. .................... 435/29 |
| 5,432,061 | 7/1995 | Berndt et al. ........................... 435/29 |
| 5,432,086 | 7/1995 | Franzl et al. ........................... 435/29 |
| 5,483,080 | 1/1996 | Tam ........................................ 435/29 |
| 5,510,246 | 4/1996 | Morgan .................................. 435/29 |
| 5,552,321 * | 9/1996 | Focht .................................. 435/283.1 |
| 5,643,742 | 7/1997 | Malin et al. ............................ 435/29 |
| 5,863,752 | 1/1999 | Court et al. ............................ 435/29 |

OTHER PUBLICATIONS

Catalona, W.J., et al., "A Multicenter Evaluation of PSA and Digital Rectal Examination (DRE) for Early Detection of Prostate Cancer in 6,374 Volunteers", *Journal of Urology*, vol. 149(Suppl.) 1993, p. 412A.

(List continued on next page.)

*Primary Examiner*—Louise N. Leary
(74) *Attorney, Agent, or Firm*—Mathews, Collins, Shepherd & Gould P.A.

(57) ABSTRACT

The present invention describes an electrooptical apparatus and method for monitoring cell growth in microbiological culture. The apparatus comprises an electrooptical cell filled up with a cell suspension and having electrodes and two orthogonal optical channels for passing through two light beams, an electrical generating means for supplying an alternating electrical current on said electrodes for inducing an alternating electrical field with predetermined frequency and strength in said electrooptical cell to give rise preferred orientation of the bacterial cells, an optical system for generating signals in response to the optical density changes in both optical channels by turning on and turning off said alternating electrical field, a temperature controlling means of the electrooptical cell, a cell suspension delivery means connected with the electrooptical cell, an electronic unit determining and displaying growth parameters of the bacterial cells. The method comprises the steps of an automated withdrawing of the cell suspension sample from the microbiological culture, a dilution in specified ratio, a delivery of the diluted cell suspension in said electrooptical cell, and acquiring optical density data of said diluted cell suspension in two orthogonal directions by turning on and off the alternating electrical field to receive an electrooptical response of the cell suspension for a plurality of the frequencies of the alternative electrical field, and calculating a cell concentration, a cell size distribution and a viable cell content in said cell suspension.

10 Claims, 6 Drawing Sheets

OTHER PUBLICATIONS

Smith, D.S. & Catalona, W.J., "Interexaminer Variability of Digital Rectal Examination in Detecting Prostate Cancer", *Urology,* Jan. 1995, vol. 45, No. 1, pp. 70–74.

Lerner, R.M., Huang, S.R., & Parker, K.J., "Sonoelasticity Images Derived from Ultrasound Signals in Mechanically Vibrated Tissues", *Ultrasound in Med & Biol.,* vol. 16, No. 3, pp. 231–239, 1990.

Krouskip, T.A., Dougherty, D.R. & Levinson, S.F., "A Pulsed Doppler Ultrasonic System for Making Noninvasive Measurements of the Mechanical Properties of Soft Tissue", *Journal of Rehabilitation Research and Development,* vol. 24, No. 2, 1987, pp. 1–8.

Yoshiki Yamakoshi, Junichi Sato & Takuso Sato, "Ultrasonic Imaging of Internal Vibration of Soft Tissue Under Forced Vibration", *IEEE, Transactions on Ultrasonics, Ferroelectrics, and Frequency Control,* vol. 37, No. 2, Mar. 1990, pp. 45–53.

Littrup, P.J., Goodman, A.C. & Mettlin, C.J., "The Benefit and Cost of Prostate Cancer Early Detection", *CA–A Cancer Journal for Clinicians,* vol. 43, No. 3, Jun. 1993, pp. 134–149.

Bohren, C.F. & Huffman, D.R., "Absorption and Scattering of Light by Small Particles", Chapter 7, *"Geometrical Optics"* Wiley Science Paperback Series, John Wiley & Sons, Inc., 1998, pp. 166–171.

Van de Hulst, H.C., "Light Scattering by Small Particles", Chapter 8, *"Particles Very Large Compared to the Wavelength",* Dover Publications, Inc. New York, 1957, pp. 103–109.

\* cited by examiner

ELECTROOPTICAL APPARATUS AND METHOD FOR MONITORING CELL GROWTH IN MICROBIOLOGICAL CULTURE

BACKGROUND OF THE INVENTION

1. Field of the Invention

The present invention relates generally to devices and methods for determining and/or analyzing properties of suspensions and solutions, and more particularly an apparatus and method for determining and analyzing the cell growth parameters in a liquid biological culture medium.

2. Description of the Related Art

Many industrial and laboratory processes require the periodic or continual measurements of the cell growth parameters such as cell concentration, cell size distribution and relative quantity of viable cell suspended in liquid or in culture medium. These data are critical to the proper control of variables which influence cell growth rate (e.g. temperature, pH, nutrient levels, etc.).

Modern advancements in the science of recombinant gene technology have given rise to new possibilities for large scale production of difficult to synthesize chemical substances, through the controlled fermentation or culture of genetically recombinant microorganisms, as well as "wild type" microorganisms. The industrial fermentation or culture of genetically recombinant microorganisms is typically effected by growing the recombinant microorganisms under aseptic conditions within a liquid growth medium contained in a bioreactor or fermenter vessel. Such bioreactor or fermentation vessels generally comprise an enclosed vessel outfitted for microprocessor or computer effected control of variables such as feed rate, temperature, pH and oxygen content. Periodic or continuous measurements of cell density by optical method are utilized as a basis for making corresponding changes in process variables. See, e.g., L. A. Tam, Method and Device for Measuring and Controlling Cell Density in Microbiological Culture, U.S. Pat. No. 5,483,080; W. R. Mandel, A. J. Dekovich, Apparatus and Method for Optical Density Measurements of Biomass Processes, U.S. Pat. No. 4,893,935. This method gives only the information about cell or product concentration in a biological reaction system.

Another apparatus was developed for directly monitoring microorganisms in a bioreactor by a TV camera that has an optical magnifying system and a refilled sample cell for cell suspension. By analyzing the cell images on a computer program, it is possible to receive the cell sizes and cell concentration in the culture medium (T. Saito, at. al., Microorganism Monitoring Apparatus, U.S. Pat. No. 4,661,845.). This method though is expensive and does not give information about content of viable cells in suspension.

Another approach to determinate the cell concentration and cell size distribution in cell suspension is used by simultaneous measuring an optical and electrical impedance on a stream of particles or cells passing through a particle sensing aperture. This method is known as flow cytometry. In all known devices the electrical field is used only for cell sorting. See, e.g., J. D. Hollinger, R. I. Pedroso, Parting Analyzing and Sorting Apparatus, U.S. Pat. No. 4,515,274; K. Yamamoto, et al., Cell Analyzer, U.S. Pat. No. 5,408,307.

To monitor the growth of microorganisms in liquid culture another method is used comprising the detection of pressure change in a gas-tight container incorporating a flexible diaphragm. See, e.g. N. T. Court, et al. Method and Apparatus for Monitoring the Growth of Microorganisms in Liquid Culture, U.S. Pat. No. 5,863,752.

An apparatus is known that comprises electrodes which can be introduced into a cell culture sample for measuring an electrical impedance of the suspension. The growth or multiplication of microorganisms is determined in terms of the impedance measurements. See, e.g. G. Franzi, Apparatus for the Automatic Monitoring of Microorganism Culture, U.S. Pat. No. 5,432,086; P. J. Malin et al. System for Electronically Monitoring and Recording Cell Culture, U.S. Pat. No. 5,643,742.

It has been proposed to detect the presence or absence of living microorganisms by treating the cell suspension special chemical markers of fluorochromes and monitoring light emission produced by cell suspension. Viable and nonviable cells have the different specificity for the markers and accordingly emit or do not emit the light. (J. R. Clendenning, Method and Detecting Living Microorganisms, U.S. Pat. No. 3,933,592; J. W. Steele, F. Sribnik, Automated Bilumi-nescence Microbial Monitor, U.S. Pat. No. 5,141,869.) The classical method of determination of viable cell quantity in culture is early detection and enumeration of colonies in the growth medium (S. D. Morgan, Method for Rapid Quantification of Microorganism Growth, U.S. Pat. No. 5,510, 246).

In general, it is known that when living cells are disposed in a liquid and the liquid is placed in alternating electrical field, the cells will tend to be oriented in the field, even if the dielectric properties of the cells and surrounding medium are isotropic. Due to the nonspherical shape of microbial cells, the mean potential energy of the system depends on the orientation of the cells with respect to the field. The direction corresponding to the minimum energy determines the stable state of orientation. For instance, for pure and isotropic dielectrics, it is well known that an ellipsoidal body always will be oriented with its longest axis parallel to the external field. Electrooptical Apparatus for Microbial Identification and Enumeration, described in U.S. Pat. No. 4,576,916 by G. E. Lovke and R. J. Meltzer, uses this cell orientation phenomena. The main destination of this device is the optical identification of microorganisms by low-frequency electrical field (<1 kHz). It should be noted that the high requirements for accuracy and stability of a electrooptical device by work with biological objects was not realized in a sufficient value in the known equipment.

SUMMARY OF THE INVENTION

The invention provides an electrooptical apparatus and method which takes advantage of the Kerr Effect to detect, monitor, measure and utilize the affects of electric fields.

The present invention describes an electrooptical apparatus and method for monitoring cell growth in microbiological culture. An apparatus performs the calculation in real-time of the cell growth parameters such as cell concentration, cell size distribution, and relative quantity of viable cell suspended in culture medium. For this purpose, a cell suspension sample is withdrawn automatically from a biological reactor or fermenter, diluted to specified optical density, and delivered into an electrooptical cell, having paired electrodes and two orthogonal optical channels for passing through two light beams. The present invention provides an electrooptical apparatus in which the optical density changes of suspension are measured in two orthogonal directions by inducing in electrooptical cell of an alternating electrical field in frequency range from 1000 Hz up to 100 MHz for determining an electrooptical cell response for a plurality of frequencies.

The present invention also provides an electrooptical apparatus in which the optical density changes can be simultaneously and precisely measured in two orthogonal directions for cell relaxation from partially oriented state to random state after turning off an electrical field.

In addition, the present invention provides an electrooptical apparatus in which an optimal measurement condition can be adjusted for each sample so as to increase the reliability of obtained results and to measure a large number of samples with high efficiency.

The invention will be more fully described by reference to the following drawings.

DETAILED DESCRIPTION

Figure 1:
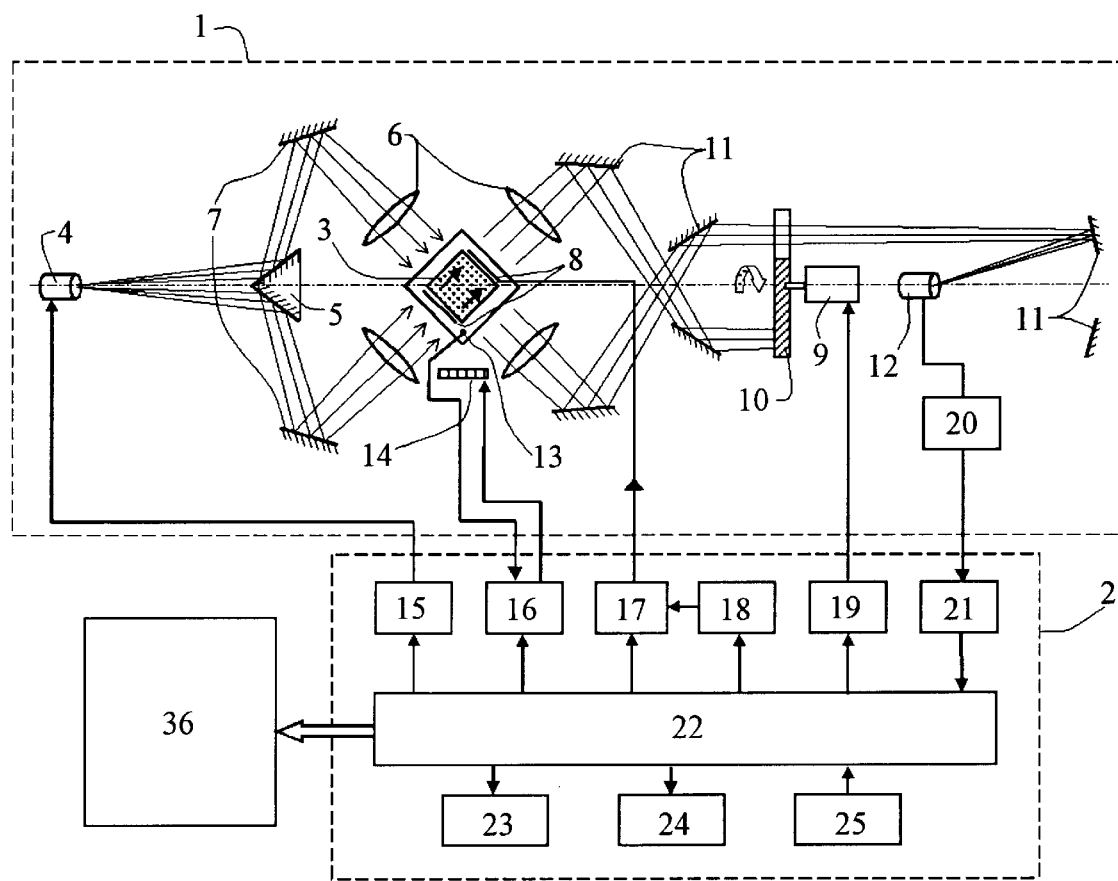
FIG. 1 is a schematic diagram of the electrooptical apparatus of the preferred embodiment of the present invention.

Reference will now be made in greater detail to a preferred embodiment of the invention, an example of which is illustrated in the accompanying drawings. Wherever possible, the same reference numerals will be used throughout the drawings and a description to refer to the same or like parts.

The detailed description set forth below in connection with the appended drawings is intended merely as a description of the presently preferred embodiments of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent function and sequences may be accomplished by different embodiments and may be satisfactory applied for the measurement of any suspension or solution which may exhibit similar behavior that are also intended to be encompassed within the spirit and scope of the invention.

The term "electrooptical response" as used in this disclosure, refers to the alternating electrical field-induced shift in light intensity of transmitted cell suspension beams which results from preferred cell orientation in suspension.

A preferred embodiment of an electrooptical apparatus is shown in FIG. 1. The apparatus comprises three parts: electrooptical assembly 1, electronic unit 2 and preparation unit 36. Electrooptical assembly 1 comprises electrooptical cell 3 filled up with a cell suspension and having electrodes 8 for establishing an induced electrical field inside electrooptical cell 3 along an optical channel as it is shown by thicken arrows. An electrical generating means for supplying an alternating electrical current on electrodes 8 includes a generator 18 connected to a power amplifier 17. Generator 18 as well as power amplifier 17 are controlled by processor 22 in accordance with an operating instructions. Generator 17 provides harmonic electrical oscillations in the range 0.001–100 MHz. Power amplifier 17 supplies a specified alternating voltage strength to electrodes 8 for a predetermined time interval. Power amplifier 17 is turned on and off for turning on and off the alternating electrical field.

By precise electrooptical measurements, the temperature of the cell suspension under investigation has to be kept up at a definite value. For this purpose, and for protection of the cell suspension against overheating, electrooptical 1 apparatus comprises a temperature controlling means including temperature sensor 13, heating/cooling element 14 and temperature controller 16.

Referring again to FIG. 1, optical assembly 1 also includes light source 4, wedge-shaped mirror 5 for forming two light beams from light source 4, and mirrors 7 for irradiating light beams onto electrooptical cell 3 in two orthogonal directions. The amount of radiation energy that light source 4 emits is controllable by varying the electrical signal emitted by controller 15 in the accordance with an appropriate command of processor 22. The light intensity of light source 4 is selected for every type of analyzed cells going from an optimal maintenance of the electrooptical signal to noise ratio. A light source can be used as laser or light diode. For example, by analysis of a plurality type of bacterial cells the good results were received by using light diode with a wavelength 680 nanometers. Optical assembly 1 further includes mirrors 11 and lenses 6 for focusing transmitted electrooptical cell orthogonal beams to a light detector 12. Lenses 6 also provide parallelism of the light beam inside electrooptical cell 3. Light detector 12 is connected to high-precision amplifier 20. The amplified signal is received at analog-to-digit converter 21 and passed to processor 22. A suitable light detector 12 is a photodiode, however, other types of light detectors known in the art could be used. To separate the signals from two light beams passed through electrooptical cell 3, electromechanical modulator 9 with rotating shutter 10 is used for alternate beam chopping of the light beams passing through electrooptical cell 3. A controller 19 provides operating control of electromechanical modulator 9 controller 19. Controller 19 is connected to processor 22.

Electronic unit 2 also includes displaying device 23, storage device 24, and control unit 25. Display device 23 is connected to processor 22, thereby displaying the cell monitoring process, and the results of the measurement and analysis. Storage device 24 is used for storing the results of the cell analysis generated processor 22. Control unit 25 is connected to processor 22 for controlling the cell operation end measurement process.

The advantage of above described optical system consists in using one transmitting source and one detecting means by measuring small unlike-directed optical shifts in two light beams passed through cell suspension, and what is more by synchronous filtration on the frequency of modulation, it is possible to receive high-precision measurements of the electrooptical response.

Figure 2A:
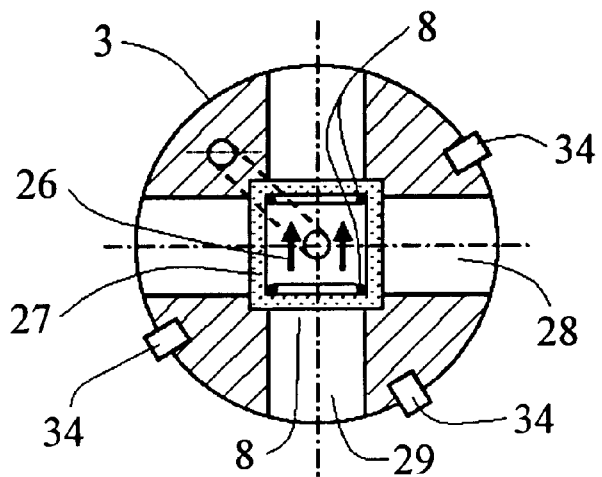
FIG. 2A is a horizontal cross-sectional view of the electrooptical cell of the electrooptical apparatus.
Figure 2B:
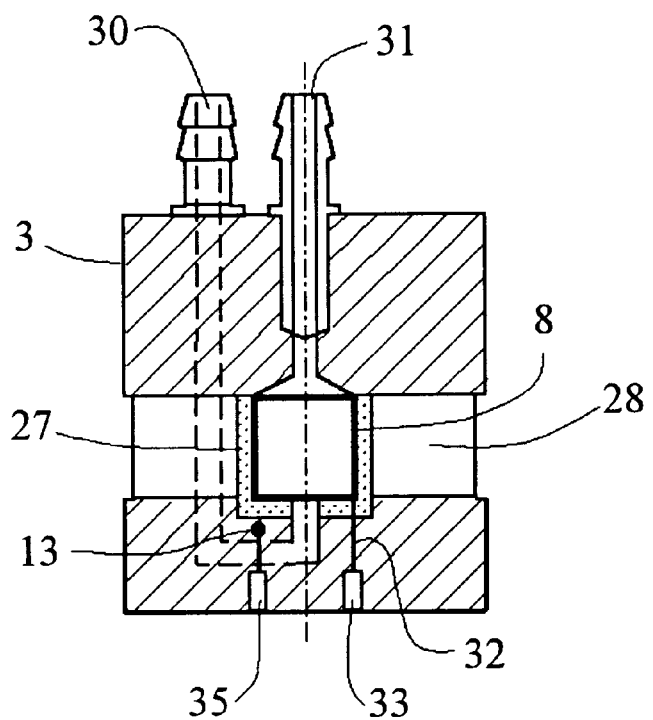
FIG. 2B is a vertical cross-sectional view of the electrooptical cell of the electrooptical apparatus.

Referring to FIGS. 2A and 2B, electrooptical cell 3 comprises transparent cubic cuvette 27 preferably made from glass or quartz and having inlet 30 and outlet 31 for cell suspension, two orthogonal optical channels 28 and 29, paired electrodes 8, temperature sensor 13, and guide shoes 34 for precise installation the electrooptical cell in the electrooptical assembly. Electrodes 8 are placed inside cuvette 27 perpendicular to the light beam of optical channel 29 in order to provide induced electrical field parallel to optical channel 29 as it is shown by thicken arrows 26. Preferably each electrode 8 is produced in the form of a square wire frame. Another preferred electrode form is a fine-wire flat lattice adjacent to the inner wall of cuvette 27. One pair of the fine-wire lattices is used for inducing electrical field along optical channel 29, another pair of identical fine-wire lattices (not shown) is located in optical channel 28 to make identical both optical channels 28 and 29 for orthogonal light beams passing through. The electrical field applied between electrodes 8 may vary in intensity, and is preferably a field strength sufficiently high to provide a weak partial cell orientation enough for precise electrooptical measurements and sufficiently low to prevent translational movement of the cell and formation of cell aggregates (pear chain formation). For this purpose the optimal field strength is determined for each type of cells. Electrooptical cell 3 further comprises electrical connection 33 for electrodes 8 and electrical connection 35 for temperature sensor 13.

Figure 3:
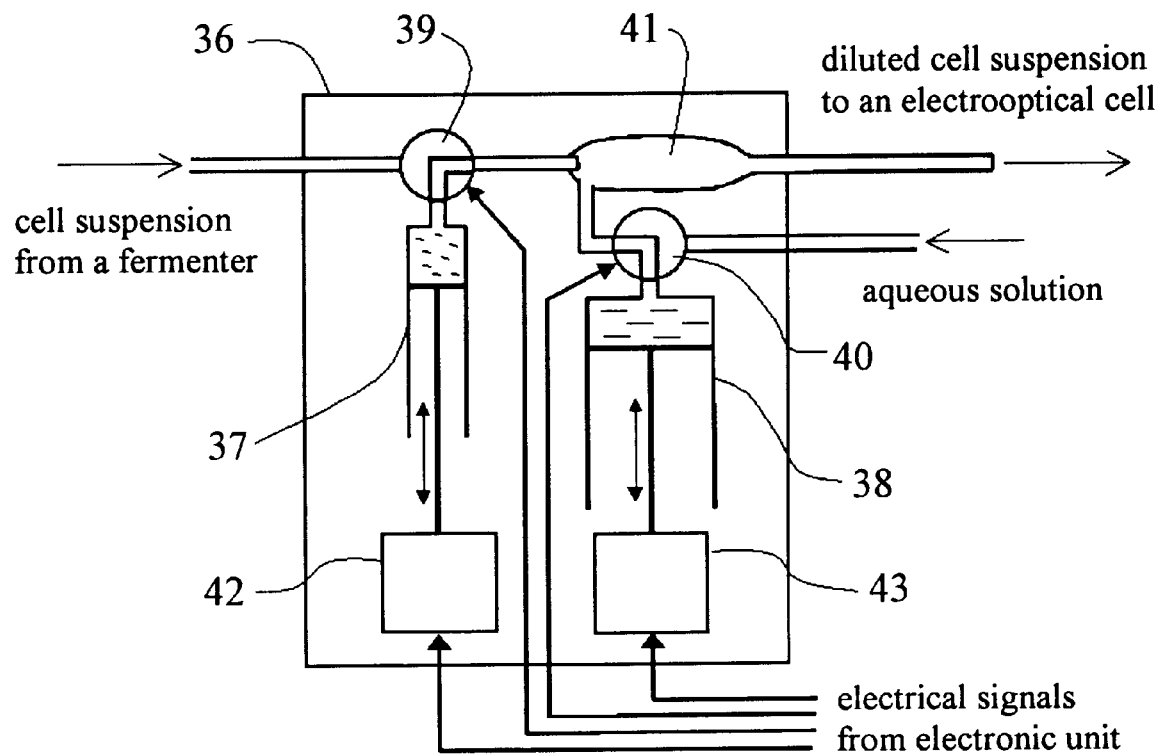
FIG. 3 is a schematic diagram of a preparation unit.

Referring to FIG. 3, preparation unit 36 shown in more detail comprises syringe infusion pump 37 for withdrawal of a cell suspension sample from a bioreactor or fermenter and for delivery of the sample into mixing chamber 41, syringe infusion pump 38 for delivering aqueous solution into mixing chamber 41 and for further delivery of a diluted cell suspension into the electrooptical cell. Syringe infusion pumps 37 and 38 are controlled by processor 22 (shown in FIG. 1) through respective operation controllers 42 and 43. Three-way direct lift solenoid valves 39 and 40 are also controlled by processor 22 in accordance with an operation mode. The positions of valves 39 and 40 corresponding the mixing mode with simultaneous delivery diluted cell sample into electrooptical cell is shown in FIG. 3. A specified dilution ratio is assigned by the flow rate ratio aqueous solution from pump 38 to cell suspension sample from pump 37. A sucrose solution or distilled water can be used for some cell types as the aqueous solution. Preparation unit 36 can be also used for washing electrooptical cuvette 27 after measurement is complete.

Figure 4:
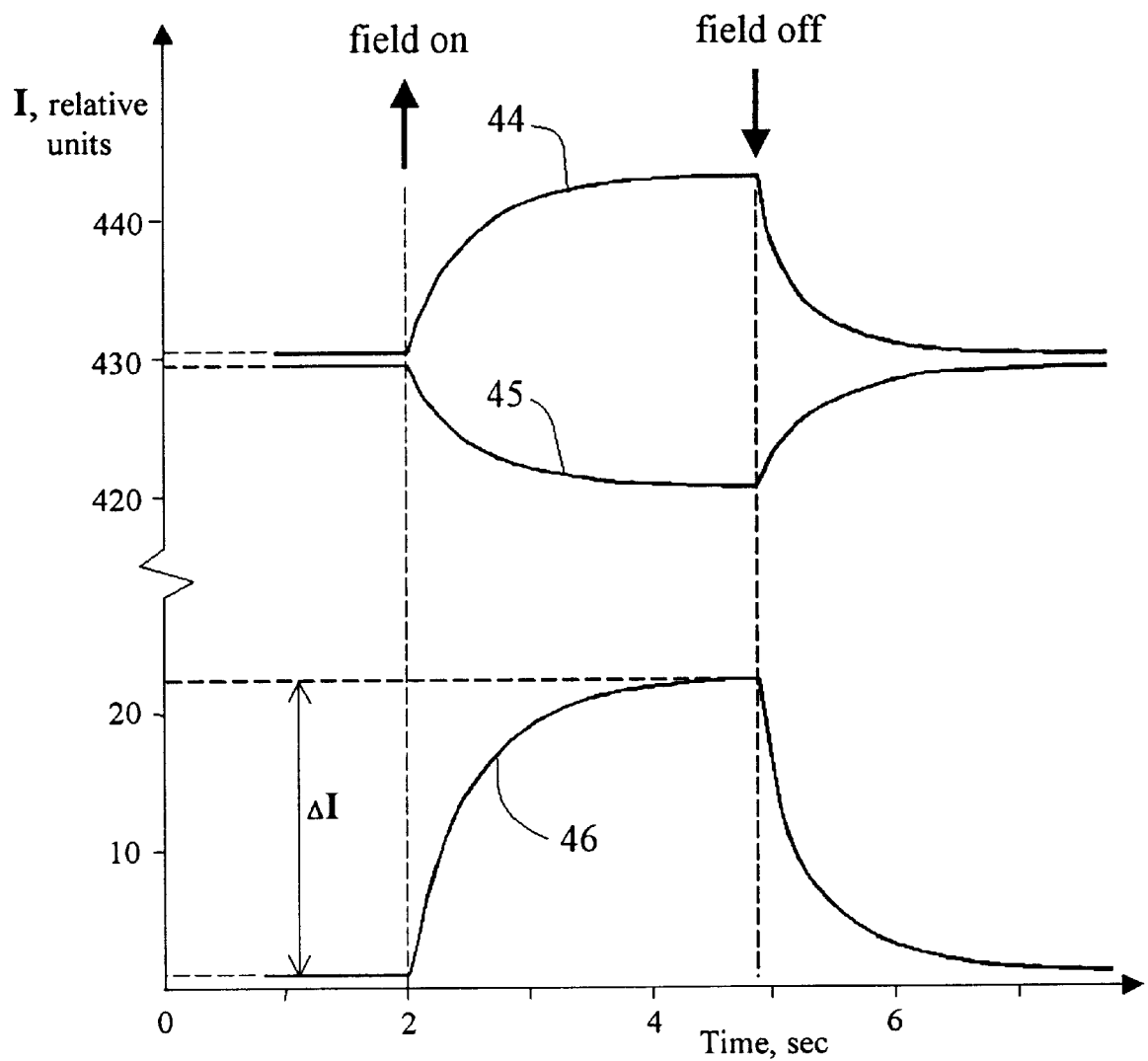
FIG. 4 is a graph showing time dependence of the light intensity of orthogonal transmitted beams and its difference for cell suspension in the electrooptical cell by turning alternating electric field on and off.

FIG. 4 shows three graphs with plots of light intensity versus time obtained using an electrooptical apparatus by testing bacteria Listeria according to the present invention. The upper chart 44 represents the light beam intensity passed through optical channel 29. By turning the electrical field on, the analyzed cell suspension becomes more transparent in the direction of applied field 26, and less transparent in orthogonal direction due to the cell orientation along the electrical field. Decreasing the light beam intensity passed through orthogonal optical channel 28 demonstrates this effect and is shown on plot 45. After turning electrical field off plots 44 and 45 show the cell relaxation process from preferred oriented state to original random state. Plot 46 is the difference between plots 44 and 45. A value ΔI is namely the electrooptical response.

Figure 5A:
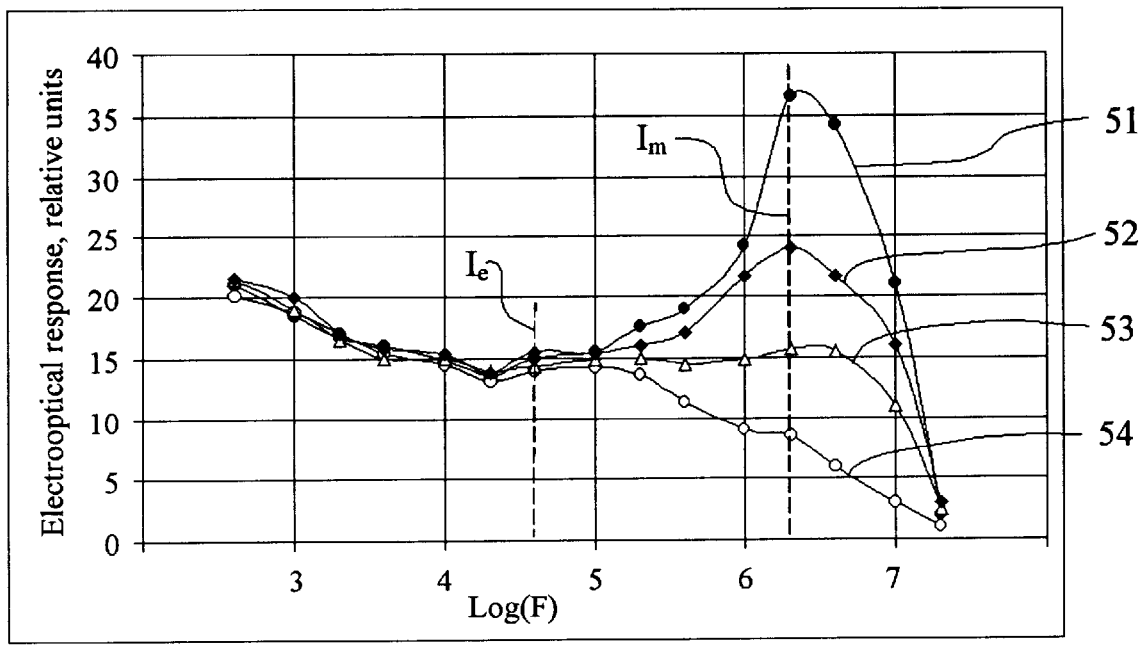
FIG. 5A is a graph showing an example of the electrooptical responses depending on the frequency of the electric field for different content of the viable cells in suspension.
Figure 5B:
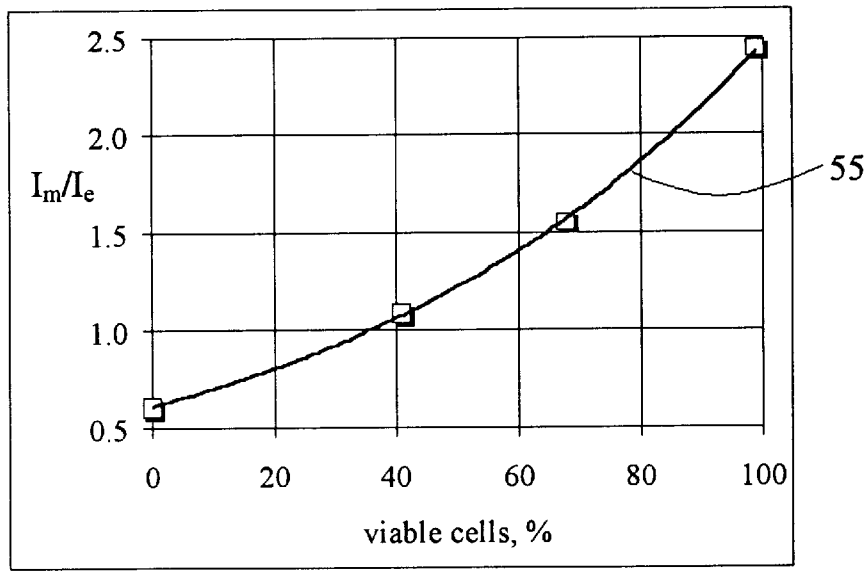
FIG. 5B is a graph showing the ratio of the electrooptical responses for two frequencies vs. the viable cell content.

To determine a viable cell content in culture a set of calibration experiments with cell suspensions containing different concentrations viable and nonviable cells have to be performed. Concentration of viable and nonviable cells in these experiments has to be established independently, for example, from light microscopic measurements. These calibration experiments allow the determination frequencies by which the ratio of electrooptical responses correlates with viable cell content. FIG. 5A shows charts with plots of electrooptical responses versus electrical field frequencies obtained using an apparatus according to the present invention for different relative quantity of viable cells in bacteria Listeria culture. Plot 54 corresponds to viable cell content 0%, plot 53 corresponds to 42.3%, plot 52 corresponds to 67% and plot 51 corresponds to 99.1%. The value of electrooptical response on frequency 0.04 MHz $I_e$ does not practically depend from viable cell content, but the electrooptical responses on frequency 2 MHz $I_m$ demonstrates clear dependence the value of electrooptical response form the viable cell content. Practically the consideration of the ratio of electrooptical responses for these frequencies $I_m/I_e$ removes the influence of the value of optical supension density. FIG. 5B shows the graphs with plots of ratio $I_m/I_e$ versus viable cell content in cell suspension. This data can be considered as the calibration data for bacteria Listeria for determining the relative quantity of viable cells in suspension with unknown content.

Figure 6:
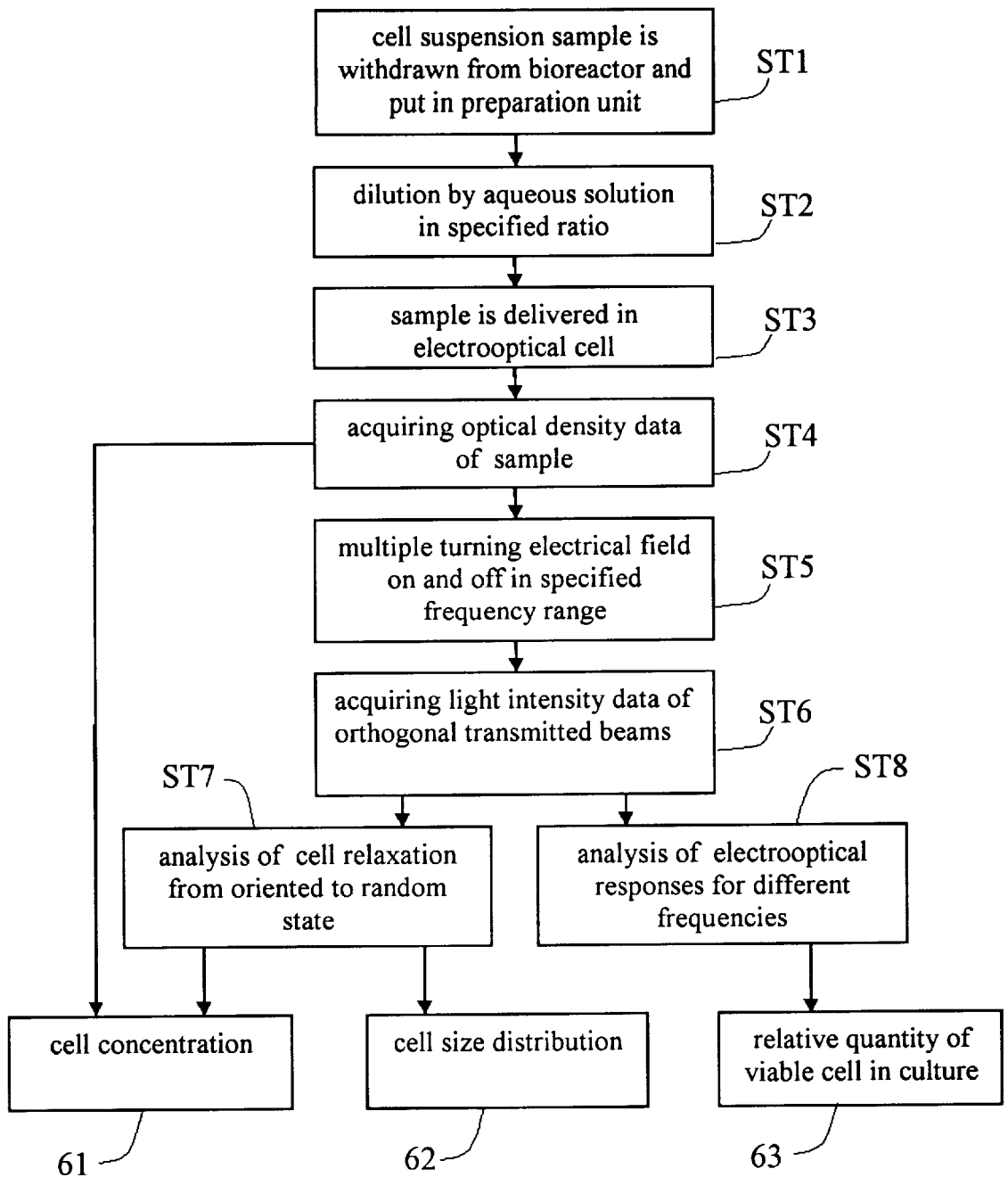
FIG. 6 shows a flow chart of a method for determining cell growth parameters in a suspension according to the present invention.

FIG. 6 is a flow chart showing the operational steps of one example of an electrooptical measuring method in accordance with the present invention. In ST1, a cell suspension sample is withdrawn from fermenter or bioreactor by preparation unit 36, then in ST2 this cell sample is diluted in specified ratio by aqueous solution and delivered in electrooptical cell 3 in ST3. For example, if a previous measurement of the optical density was about 0.3 then a dilution of 0.15 is used to provide an optical density range (about 0.05–about 0.2). In ST4, an optical density of the diluted cell suspension is measured in optical channels 28 and 29 of electro optical cell 3. Steps ST5 and ST6 are carried out simultaneously and consist in acquiring light intensity data of orthogonal transmitted beams by turning alternating electrical field on and off to receive an electrooptical response of cell suspension for a plurality of the field frequencies as is shown in FIG. 5A. For a weak cell orientation, having an orientation energy much less then energy of the thermal motion, a relaxation signal from the same size cell has the exponential view. Observed experimental relaxation signal after turning off electrical field is the sum of exponents with different exponential coefficients and weight coefficients. The exponential coefficient is proportional to a rotary diffusion coefficient which depends on cell size and viscosity of the aqueous solution. The weight coefficient is proportional to cell concentration. Analysis cell relaxation on ST7 consists of the determination of weight coefficients for the calculated rotary diffusion coefficients and verification of a constructed relaxation signal to the experimental relaxation signal. Cell size distribution 62 can be found from obtained distribution of the rotary diffusion coefficients. To determinate cell concentration 61 is determined from measured optical density on ST4 and the value of an average light scattering section of suspended cells. The value can be found by using the theory of Rayleigh-Gans-Debye as described in C. F. Bohren, D. R. Huffinan, *Absorption and Scattering of Light by Small Particles,* John Walley & Sons Publ., 1998 or anomalous diffraction theory of Van-Der-Hulst as described in H. C. Hulst, H. C. Van De Hulst, *Light Scattering by Small Particles,* Dover Publ., 1982 hereby incorporated by reference in this application. Analyzing the electrooptical responses for different frequencies on ST8, the relative quantity of viable cell in culture 63 can be obtained. The simplest way is the calculation of the electrooptical response ratio for two predetermined frequencies as is shown in FIG. 5B.

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention.

What is claimed is:

1. An electrooptical apparatus for controlling cell growth in microbiological culture comprising:

an electrooptical cell filled up with a cell suspension and having electrodes and two orthogonal optical channels for passing through two light beams;

a light source for irradiating light beams onto said electrooptical cell in two orthogonal directions;

electrical generating means for supplying an alternating electrical current on said electrodes for inducing an alternating electrical field with predetermined frequency and strength in said electrooptical cell to provide orientation of bacterial cells of the microbiological culture;

optical system focusing two perpendicular light beams passed through said electrooptical cell to a light detector and for generating signals in response to the optical density changes in said perpendicular light beams by turning on and turning off said alternating electrical field;

temperature controlling means for controlling the temperature of said electrooptical cell;

cell suspension delivery means connected to said electrooptical cell for delivering said and cell suspension to said electrooptical cell;

an electronic unit receiving said signals from said optical system, controlling said electrical generating means and said cell suspension delivery means, determining and displaying growth parameters of said bacterial cells.

2. The apparatus of claim 1 wherein said electrooptical cell comprises:

a pair of frame wire electrodes to induce said alternating electrical field along one of said optical channel inside said electrooptical cell.

3. The apparatus of claim 1 wherein said electrooptical cell further comprises:

a temperature sensor for measuring the temperature of said cell suspension.

4. The apparatus of claim 1 wherein said optical system comprises:

a mechanical modulator for an alternate beam chopping of said light beams passed through said electrooptical cell.

5. The apparatus of claim 1 wherein said cell suspension delivery means comprises:

a mixing chamber and at least two syringe pumps electrically connected to said electronic unit for dilution of said cell suspension in specified ratio by a aqueous solution.

6. An electrooptical method for controlling cell growth in microbiological culture comprising the steps of:

automated withdrawing of a cell suspension sample from said microbiological culture;

diluting of said cell suspension sample in a specified ratio by an aqueous solution;

delivering of a diluted cell suspension in to a electrooptical cell;

measuring an optical density of said diluted suspension in said electrooptical cell;

acquiring light intensity data of orthogonal transmitted beams by turning alternating electrical field on and off to receive an electrooptical response of said diluted cell suspension for a plurality of the frequencies of said alternating electrical field; and calculating a cell concentration, a cell size distribution and a viable cell concentration in said cell suspension.

7. The method of claim 6 wherein said dilution is realized so that an optical density of said diluted cell suspension is in the range of about 0.05 to about 0.2.

8. The method of claim 6 wherein said plurality of frequencies are in the range of about 0.001 to about 100 MHz.

9. The method of claim 6 wherein said step of calculating a cell size distribution comprises the step of:

analyzing of a cell relaxation from an oriented state into a random state using said acquired light intensity data after turning off said alternating electrical field.

10. The method of claim 6 wherein said step of calculating a viable cell concentration comprises the step of:

calculating a ratio of said electrooptical responses for two specified frequencies of said alternative electrical field.

* * * * *